United States Patent
Hagn et al.

(10) Patent No.: US 10,085,806 B2
(45) Date of Patent: Oct. 2, 2018

(54) MINIMALLY INVASIVE INSTRUMENT FOR ROBOTIC SURGERY

(71) Applicant: DEUTSCHES ZENTRUM FÜR LUFT-UND RAUMFAHRT E.V., Köln (DE)

(72) Inventors: Ulrich Hagn, München (DE); Georg Passig, Kosching (DE); Sophie Lantermann, München (DE); Florian Fröhlich, Germering (DE); Ulrich Seibold, Burnaby (CA)

(73) Assignee: DEUTSCHES ZENTRUM FÜR LUFT-UND RAUMFAHRT E.V., Köln (DE)

( * ) Notice: Subject to any disclaimer, the term of this patent is extended or adjusted under 35 U.S.C. 154(b) by 492 days.

(21) Appl. No.: 14/399,116

(22) PCT Filed: Apr. 30, 2013

(86) PCT No.: PCT/EP2013/058996
§ 371 (c)(1),
(2) Date: Nov. 5, 2014

(87) PCT Pub. No.: WO2013/167427
PCT Pub. Date: Nov. 14, 2013

(65) Prior Publication Data
US 2015/0150636 A1 Jun. 4, 2015

Related U.S. Application Data

(60) Provisional application No. 61/711,891, filed on Oct. 10, 2012.

(30) Foreign Application Priority Data

May 9, 2012 (DE) .................. 10 2012 207 703

(51) Int. Cl.
A61B 17/00 (2006.01)
A61B 19/00 (2006.01)
(Continued)

(52) U.S. Cl.
CPC .......... *A61B 19/2203* (2013.01); *A61B 34/30* (2016.02); *B25J 1/12* (2013.01);
(Continued)

(58) Field of Classification Search
CPC ............ A61B 19/2203; A61B 34/30; A61B 2017/00535; A61B 2034/305;
(Continued)

(56) References Cited

U.S. PATENT DOCUMENTS 8,146,790 B2 * 4/2012 Milliman ............. A61B 17/115
227/175.2
2002/0062136 A1 * 5/2002 Hillstead .......... A61B 17/07207
606/205

(Continued)

FOREIGN PATENT DOCUMENTS

EP 1 779 801 A2 5/2007
EP 1779801 A2 5/2007
(Continued)

OTHER PUBLICATIONS

International Preliminary Report on Patentability dated Nov. 11, 2014, including the Written Opinion of the International Searching Authority, for International Application No. PCT/EP2013/058996 (10 pages).

(Continued)

*Primary Examiner* — Son Dang
(74) *Attorney, Agent, or Firm* — Maier & Maier, PLLC

(57) ABSTRACT

Minimally invasive instrument for robotic surgery including a functional element, a force, torque and/or pressure transmission device for transmitting force, torque and/or pressure (Continued)

from a drive to the functional element, a coupling device for coupling the instrument to a medical robot such that the functional element can be actuated by the drive, wherein an operating element for manually operating the functional element in a state in which the instrument is uncoupled from the medical robot.

3 Claims, 4 Drawing Sheets

(51) Int. Cl.
  *B25J 1/12* (2006.01)
  *B25J 13/02* (2006.01)
  *G05B 15/02* (2006.01)
  *A61B 34/30* (2016.01)
  *A61B 17/062* (2006.01)

(52) U.S. Cl.
  CPC .............. *B25J 13/02* (2013.01); *G05B 15/02* (2013.01); *A61B 17/062* (2013.01); *A61B 2017/00367* (2013.01); *A61B 2017/00464* (2013.01); *A61B 2017/00477* (2013.01); *A61B 2017/00535* (2013.01); *A61B 2034/305* (2016.02)

(58) Field of Classification Search
  CPC ........ A61B 2017/00477; A61B 17/062; A61B 2017/00464; G05B 15/02; B25J 1/12; B25J 13/02
  See application file for complete search history.

(56) References Cited

U.S. PATENT DOCUMENTS

| | | | | |
|---|---|---|---|---|
| 2003/0045900 A1* | 3/2003 | Hahnen | ............ | A61B 17/07207 606/205 |
| 2004/0116855 A1* | 6/2004 | Popov | ............... | A61M 25/0606 604/110 |
| 2005/0209624 A1* | 9/2005 | Vijay | ................. | A61B 17/3201 606/174 |
| 2007/0005045 A1* | 1/2007 | Mintz | .................... | B25J 9/0084 606/1 |
| 2007/0016174 A1* | 1/2007 | Millman | ............. | A61M 1/0058 606/1 |
| 2007/0119274 A1* | 5/2007 | Devengenzo | ............ | B25J 15/04 74/490.01 |
| 2007/0198008 A1* | 8/2007 | Hauck | .................. | A61B 5/6885 606/41 |
| 2009/0031842 A1* | 2/2009 | Kawai | .................... | A61B 17/29 74/490.01 |
| 2009/0254083 A1* | 10/2009 | Wallace | ............. | A61B 18/1482 606/41 |
| 2009/0312756 A1* | 12/2009 | Schlesinger | ....... | A61B 18/1492 606/41 |
| 2010/0262162 A1* | 10/2010 | Omori | ................ | A61B 1/00149 606/130 |
| 2011/0196419 A1* | 8/2011 | Cooper | .............. | A61B 18/1445 606/206 |
| 2011/0295260 A1* | 12/2011 | Oren | .................. | A61B 17/1714 606/80 |
| 2012/0190981 A1* | 7/2012 | Harris | .................... | A61B 34/30 600/439 |
| 2012/0245141 A1* | 9/2012 | Thomas | ............... | C07D 295/26 514/210.19 |
| 2012/0245414 A1* | 9/2012 | Verbeek | ............. | A61B 17/2909 600/106 |
| 2012/0323077 A1* | 12/2012 | Verbeek | ............. | A61B 1/00071 600/146 |
| 2013/0053866 A1* | 2/2013 | Leung | .................... | B25J 9/1689 606/130 |
| 2013/0131666 A1* | 5/2013 | Atwell | ............ | A61B 17/00234 606/41 |
| 2013/0150842 A1* | 6/2013 | Nau, Jr. | .............. | A61B 18/1445 606/13 |
| 2013/0193188 A1* | 8/2013 | Shelton, IV | ......... | A61B 17/068 227/175.2 |
| 2013/0231682 A1* | 9/2013 | Barwinkel | ......... | A61B 1/00135 606/130 |
| 2013/0245647 A1* | 9/2013 | Martin | ............... | A61B 17/0469 606/147 |
| 2013/0325057 A1* | 12/2013 | Larson | ............... | A61B 18/1445 606/205 |

FOREIGN PATENT DOCUMENTS

| | | |
|---|---|---|
| EP | 2 286 756 A1 | 2/2011 |
| KR | 2011 0003229 A | 1/2011 |
| KR | 20110003229 A | 1/2011 |

OTHER PUBLICATIONS

Sophie Thielmann et al; MICA—A New Generation of Versatile Instruments in Robotic Surgery; Institute of Robotics and Mechatronics, German Aerospace Center; 8 pgs.

International Search Report and Written Opinion dated Jul. 29, 2013 from corresponding International Patent Application No. PCT/EP2013/058996; 12 pgs.

German Office Action dated Jan. 24, 2013, in connection with corresponding DE Application No. 10 2012 207 707.3 (12 pgs.).

* cited by examiner

MINIMALLY INVASIVE INSTRUMENT FOR ROBOTIC SURGERY

FIELD

The invention relates to a minimally invasive instrument for robotic surgery.

BACKGROUND

In the minimally invasive robot-assisted telesurgery endoscopic manipulation instruments, such as grippers, needle holders etc., are operated at robot arms. An exemplary scenario is shown in FIG. 11. The robot arms 32 are remotely controlled by the surgeon 34 from an input station 36. Here, the endoscopic instruments 10 are fastened to the robot arms 32 located outside the patient's body and are simultaneously inserted into the patient's body via an incision, for example a trocar 38 in the body cavity of the patient 40. The actual surgery is carried out inside the body. Here, the endoscopic instruments 10 comprise functional instrument tips, such scissors, forceps, needle holders etc. not shown in FIG. 11. In the present patent application, these instrument tips are referred to as functional elements.

Advantageously, this mode of surgery causes a slighter trauma of the patient since merely small incisions in the patient's body are necessary. It is thus desirable to reduce not only the size of the incisions but also their number to keep the trauma of the patient at a low level. Generally, an incision for the instrument 10 of the right hand, an incision for the instrument 10 of the left hand and an incision for the optics 42 (endoscope) are required. Depending on the scenario more or even fewer incisions may be necessary.

During surgery additional material is required inside the body. For example, frequently suture material, namely a surgical needle plus thread but also clamps, pads etc., are required.

In the configuration described above which may include e. g. three incisions in the patient's body such material must be inserted and/or removed via one of these three incisions. If the preparation of an additional incision is to be avoided, at least one of the instruments must be removed from the respective incision.

In the robotic minimally invasive surgery special minimally invasive instruments located at robot arms are used, which, in contrast to manually operated instruments (manual minimally invasive surgery), do not include any handle which the surgeon may grip or via which they can be actuated by the surgeon. The degrees of freedom of the robotic/driven instruments, for example a gripper, are controlled by drives, e. g. electric motors in the instrument or in the robot arms. In the variant stated last the torque of the drives is provided at the robot flange and tapped by the instrument with a coupling and transmitted to the degrees of freedom of the instruments.

Systems for use in the minimally invasive robot-assisted surgery are described in the following publications:

S. Thielman et al. "MICA—A new generation of versatile instruments in robotic surgery", Proc. IROS, 2010, R. Devengenzo et al. "Instrument interface of a robotic surgical system", US 2007/0119274 A1, 2007

If in systems known in the art surgical material, e. g. suture material, has to be inserted into the patient's body during surgery and no additional incision is to be made in the patient's body, the insertion must be carried out via an existing incision. One of the robotic instruments must thus be removed. After uncoupling of the instrument from the robotic system the degrees of freedom of the instrument are either no longer controllable or operable (if the actuation is carried out via a drive in the robot) or only controllable by the surgeon sitting at a remote location (if the instrument comprises its own drive). Depending of the system the degrees of freedom are either blocked or completely free. The exchange of the instruments during surgery is however normally carried out by medical support staff, for example a surgical nurse. Such medial support staff cannot grip the suture material with such an instrument outside the patient's body and then insert it together with the instrument into the patient's body.

SUMMARY

In the current clinical procedure, the robotic instrument is thus removed first. The medical support staff member grips the surgical material with a manual minimally invasive instrument outside the patient's body and inserts the surgical material with the manual instrument into the patient's body. The manual instrument is then removed and finally the robotic instrument is inserted again and fastened to the robot. This procedure is very time-consuming and complex. The entire procedure must be performed under the control and supervision of the surgeon who observes the insertion and removal with the endoscope to preclude any unintentional loss of objects in the body.

It is an object of the invention to provide a minimally invasive instrument for robotic surgery with the aid of which the surgical material can be inserted into the patient's body in a simpler and quicker manner.

The minimally invasive instrument for robotic surgery according to the invention comprises a functional element, such as a gripper and/or a needle holder, for example.

The drive by means of which the functional element is driven may be an external drive arranged outside the minimally invasive instrument. Alternatively, the drive may be arranged in or at the minimally invasive instrument.

The instrument according to the invention further comprises a force, torque and/or pressure transmission device for transmitting force, torque and/or pressure from a drive to the functional element. A force transmitting device may be a cable or a coupling rod, for example. The torque can be transmitted in a known manner via gear wheels, torsion bars etc. If a pressure transmission device is used, a pressure is hydraulically or pneumatically transmitted by a fluid from the drive to the functional element and converted there into a force and/or a torque.

The instrument according to the invention further comprises a coupling device for coupling the instrument to a medical robot. This is in particular carried out such that in the coupled state the functional element is adapted to be actuated by the drive.

The instrument according to the invention is characterized by an operating element for manually operating the functional element in a state in which the instrument is uncoupled from the medical robot.

Thus the operating element according to the invention allows the functional element to be manually operated by medical support staff in the operating theater, for example, while the minimally invasive instrument is uncoupled from the medical robot. A surgical nurse can thus separate the minimally invasive instrument from the medical robot for the purpose of inserting the surgical material into the patient's body, remove said minimally invasive instrument from the patient's body and grip the surgical material with the aid of the manually operable operating element and insert it into the patient's body. Subsequently, the minimally invasive instrument is connected with the robot such that the surgery can be continued by the surgeon.

According to the invention, the insertion of surgical material into the patient's body can thus be carried out in a quicker and simpler manner without an intermediate step of using a conventional manual tool.

The operating element may further be used to grip an object (a used pad or a needle, for example) inside the body of the patient, while the instrument is coupled with the medical robot. For this purpose, the surgeon may grip the object to be removed e. g. using his control device, whereupon the operating element is manually actuated by a medical support staff member, for example. The instrument can then be uncoupled from the robot and removed from the body of the patient.

The operating element may act upon the force, torque and/or pressure transmission device for actuating the functional element, for example. Various variants of the embodiment are described below in the present application.

In an alternative embodiment, the instrument according to the invention may comprise a gear for transmitting forces and/or torques from the drive to the functional element. Here, the operating element may act upon the gear for actuating the functional element. This embodiment, too, is described below in the present patent application.

The operating element may be a lever, for example, which is adapted to be pivoted about a pivot point fixedly connected with the instrument. The lever is adapted to be mechanically coupled with the force, torque and/or pressure transmission device via a hinge point which is spaced apart from the pivot point along the lever such that the functional element can be actuated.

Alternatively, the operating element, instead of being configured as a lever, may be adapted to be linearly displaced. This linearly displaceable operating element, too, is adapted to be mechanically coupled with the force, torque and/or pressure transmission device.

In the two embodiments described last, a latch element for retaining the operating element in a position determined by the user may be provided. Here, retaining is realized such that the user need not apply any force to the operating element.

In another alternative embodiment, the operating element is a manually operable hand wheel which acts upon the gear for actuating the functional element.

In a further alternative embodiment, the operating element is a manually operable plunger which acts upon the pressure transmission device for actuating the functional element. Said pressure transmission device is filled with a fluid for pressure transmission purposes.

In the embodiments described hitherto, the minimally invasive instruments need not comprise their own drive for actuating the functional element. Rather, said element can be actuated via an external drive in the medical robot which is adapted to be coupled with the minimally invasive instrument via the coupling device.

In another alternative embodiment, the operating element is an electric and/or electronic operating element which can generate an electric signal. Here, the minimally invasive instrument comprises its own internal drive which is adapted to be supplied with the signal from the electric and/or electronic operating element such that the internal drive for actuating the functional element acts upon the gear and/or the force, torque and/or pressure transmission device. This embodiment is particularly advantageous when the minimally invasive instrument already comprises its own drive.

Said drive may be adapted to be actuated by the electric and/or electronic operating element when the minimally invasive instrument is uncoupled from the robot. In this embodiment, too, the functional element is thus adapted to be autarkically and manually operated at the minimally invasive instrument by a medical support staff member.

Further it is possible that the operating element comprises its own force, torque and/or pressure transmission device via which the functional element is actuated. The operating element thus directly engages the functional element, for example when a cable-operated gripper is used.

In a particularly preferred embodiment, the instrument is driven by an internal drive. Additionally, the functional element is adapted to be actuated by an operating element which is directly manually actuated by a user. This may be a mechanical lever or the like, for example. In this embodiment, the operating element thus does not act upon an electric motor, for example, which actuates the functional element. Rather, the functional element is exclusively mechanically actuated by the operating element. Here, the internal drive of the instrument and/or the gear connected therewith are adapted to be driven back by the manual actuation of the operating element, in particular in a state in which the instrument is uncoupled from the robot.

In another preferred embodiment, the operating element is connected with the functional element such that an actuation of the functional element by the operating element is possible even when the instrument is fastened to the robot. Here, the operating element is coupled with the mechanism of the instrument such that it has priority over the control inputs of a surgeon. Thus a medical support staff member may at any time manually trigger the gripping of the suture material, for example, which facilitates the transition between gripping by the surgeon and gripping and removing of the instrument by the assistant.

Hereunder preferred embodiments of the invention will be explained with reference to the figures in which:

DETAILED DESCRIPTION

Figure 11:
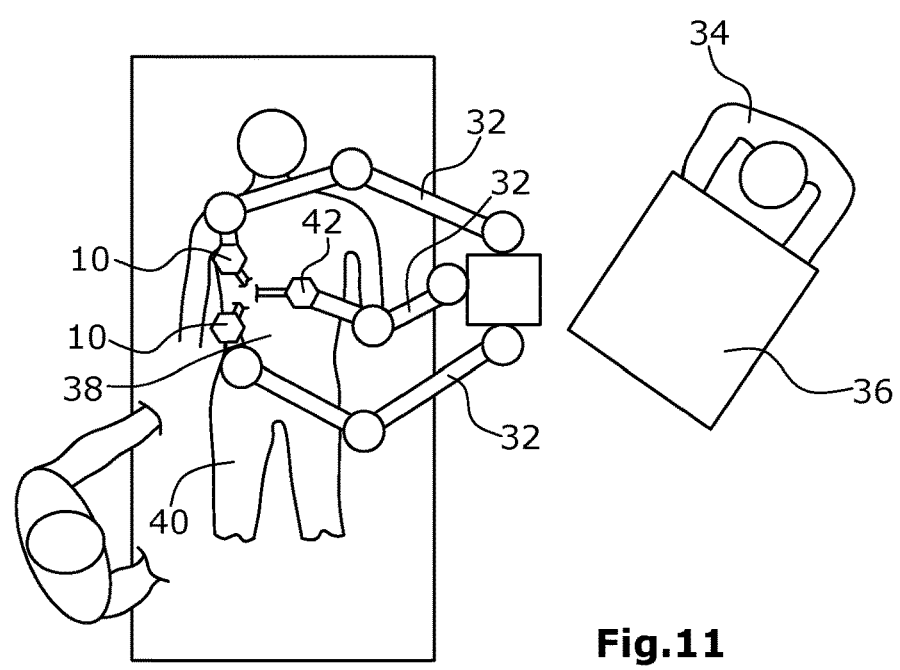
FIG. 11 shows an exemplary scenario of the robotic minimally invasive surgery.

The exemplary scenario shown in FIG. 11 of the robotic minimally invasive surgery has already been explained in conjunction with the background art in the introductory part of the description.

Figure 1:
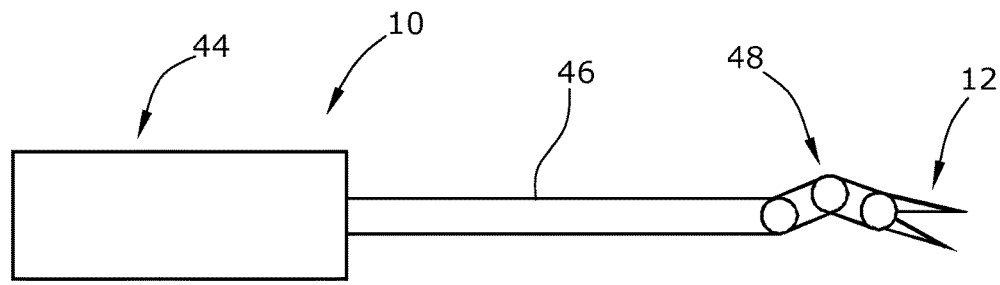
FIG. 1 shows a top view of a minimally invasive instrument.

In FIG. 1 a minimally invasive instrument 10 having a gear unit 44 is illustrated, said gear being connected via a shaft 46 and joints 48 with the functional element 12.

Figure 2:
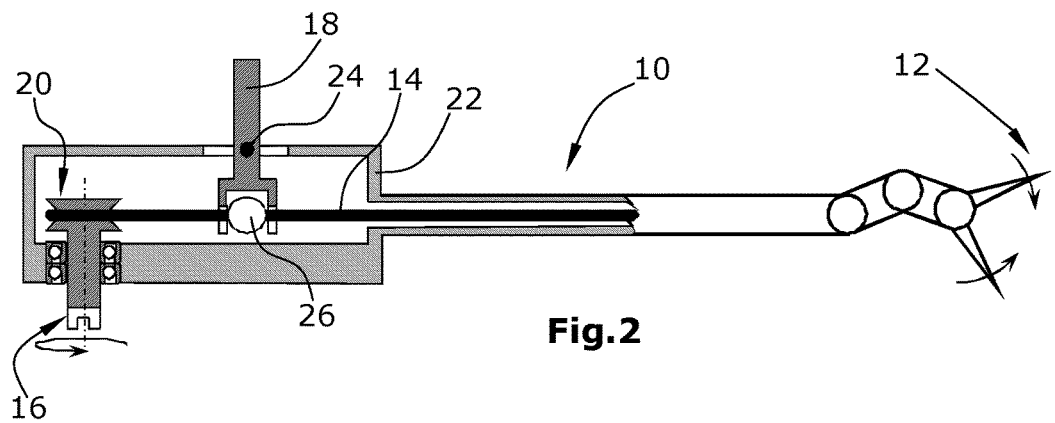
FIGS. 2 to 10 show partial sectional views of minimally invasive instruments.

An exemplary internal setup of a surgical instrument 10 is shown in FIG. 2. The surgical instrument 10 is adapted to be connected with an external drive of a medical robot via the coupling device 16. The transmitted torque is transmitted to the functional element 12 by means of a gear 20 which is connected with the functional element 12 via a cable 14, for example. If the instrument 10 is uncoupled from the medical robot the functional element 12 can no longer be actuated via the external drive. In this state a manual actuation of the functional element 12 via the operating element 18 is possible.

The latter is configured as a lever which is adapted to be pivoted about the pivot point 24 in the housing 22 of the instrument 10. The operating element 18 is coupled with the force transmission device 14 via the hinge point 26 spaced apart from the pivot point 24 along the lever 18.

Figure 3A:
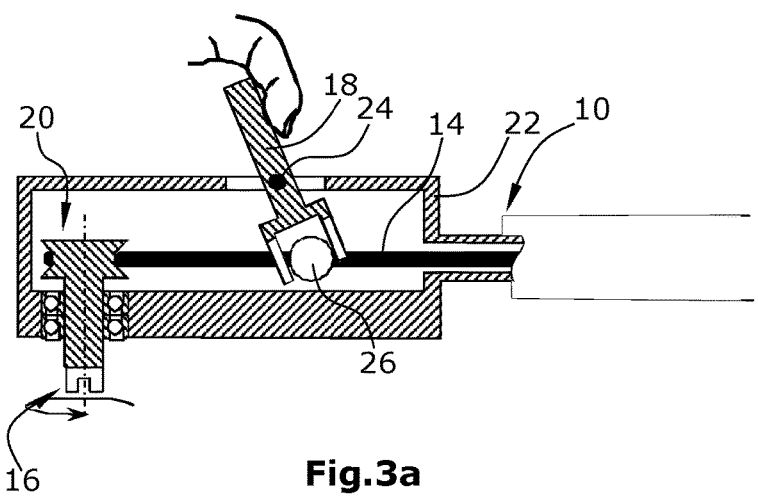
Figure 3B:
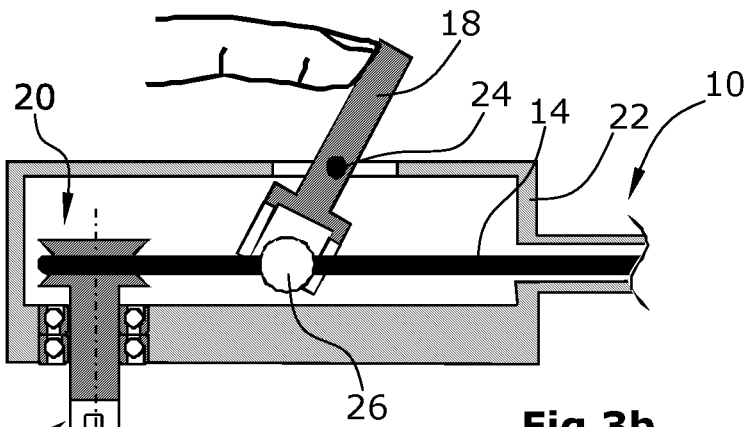

Actuation of such a lever 18 by a medical support staff member is shown in FIGS. 3a and 3b. The manual operating element 18 thus constitutes a bypass for controlling the degree of freedom of the functional element 12 via the external drive. Here, the lever 18 is mechanically coupled with the force transmission element 14 at the hinge point 26 via a ball terminal.

Figure 4:
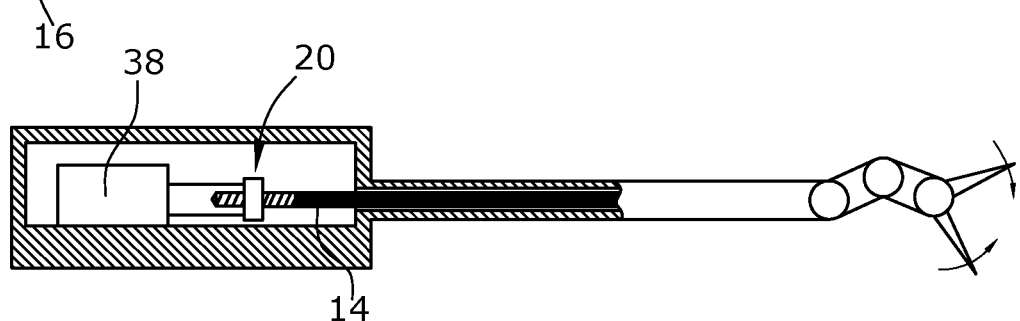
Figure 10:
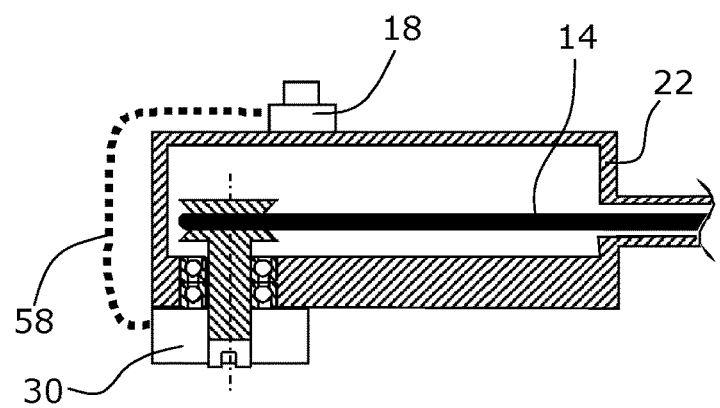

The minimally invasive instrument 10 illustrated in FIG. 4 comprises an internal drive 30 which is connected with the functional element 12 via a gear 20 and the force transmission device 14. As is illustrated in FIG. 10, this embodiment may be used for actuating the internal drive 30 via an electric and/or electronic operating element 18 such that the functional element 12 can be actuated even when the instrument 10 is uncoupled from the robot. The instrument 10 may also comprise two internal drives, wherein one drive drives the functional element 12 when the instrument 10 is coupled with the robot and the second drive serves for actuating the functional element 12 in its uncoupled state.

Alternative embodiments of the operating element 18 according to the invention are illustrated in FIGS. 5 to 9.

Figure 5:
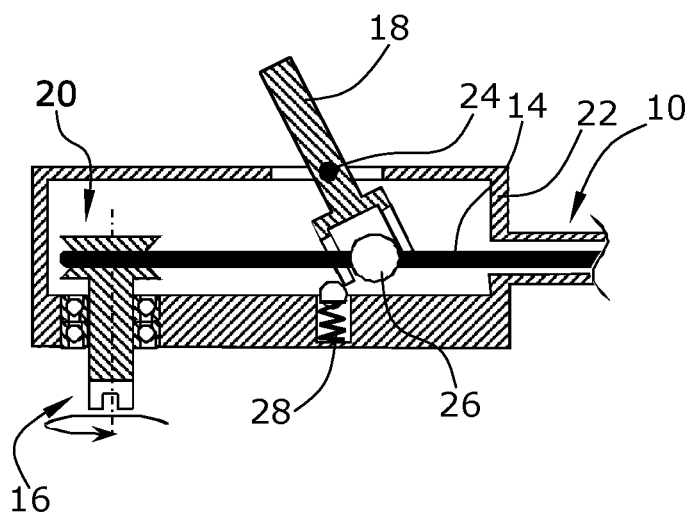

In FIG. 5 the operating element 18 is configured like the lever described above. At a suitable place, e. g. the lower side of the housing 22 of the instrument 10, a latch element 28 is provided which may be a spring-loaded ball, for example. Here, the spring force acts towards the operating element 18 such that the latch element retains the operating element in a location desired by the user without the user having to apply a pressure upon the operating element 18.

Figure 6:
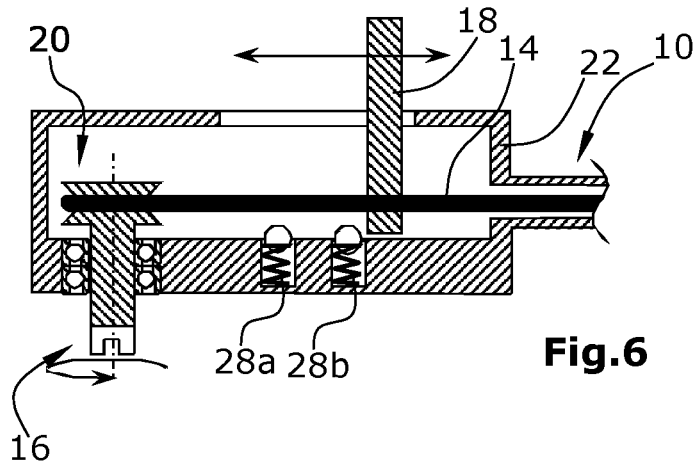

In FIG. 6 a linearly displaceable operating element 18 is illustrated which may cooperate with two latch devices 28a, 28b. The operating element 18 can thus be retained in three different positions.

In an alternative embodiment, the latch device may be defined by a positioning device in which a linearly displaceable lever 18 is displaced. This positioning device may comprise a plurality of latch positions in which the lever 18 snaps into place. Between these latch positions the lever is adapted to move freely.

Figure 7:
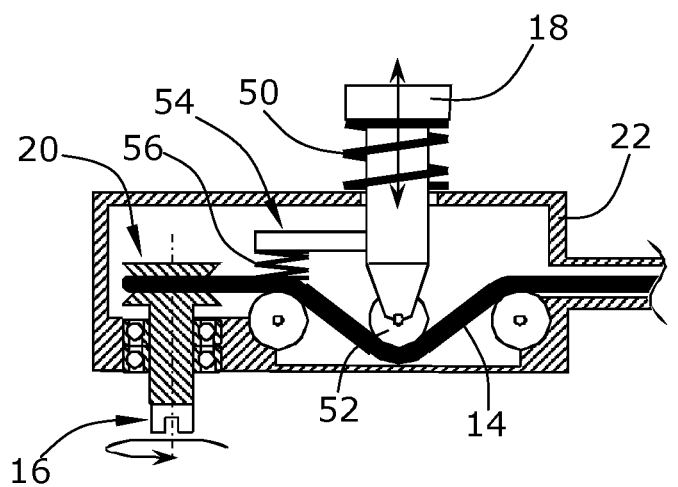

The operating element 18 illustrated in FIG. 7 is also adapted to be linearly displaced. This linear displacement is however effected in a substantially vertical direction relative to the direction of extension of the force transmission element 14. The operating element 18 rests with a spring 50 at the housing 22, for example. At the lower end the operating element 18 preferably comprises a roller 52 which acts upon the force transmission device 14. If the force transmission device 14 is constituted by one or more cables the roller 52 may simultaneously act upon several cables to actuate the functional element. Further, this operating element 18 preferably comprises a clamping device 54 which defines, by means of a spring 56, the gear-side end of the force transmission device 14, for example a cable, such that the actuation of the operating element 18 has exclusively an effect on the shaft-side cable end.

Figure 8:
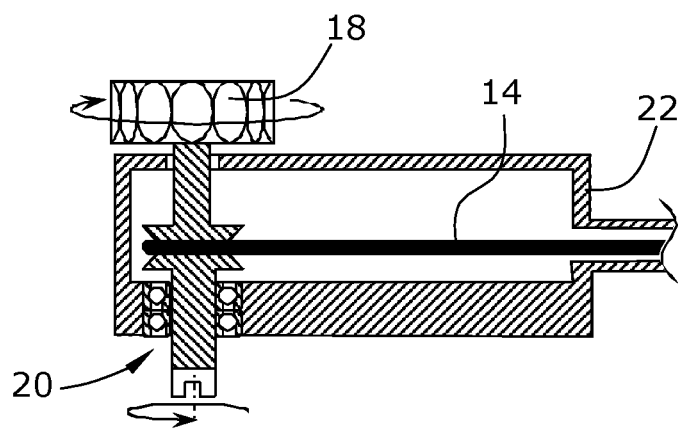

In FIG. 8 the operating element 18 is configured as a hand wheel which directly acts upon the gear 20. Thus the hand wheel 18 is turned for opening and closing the functional element 12.

Figure 9:
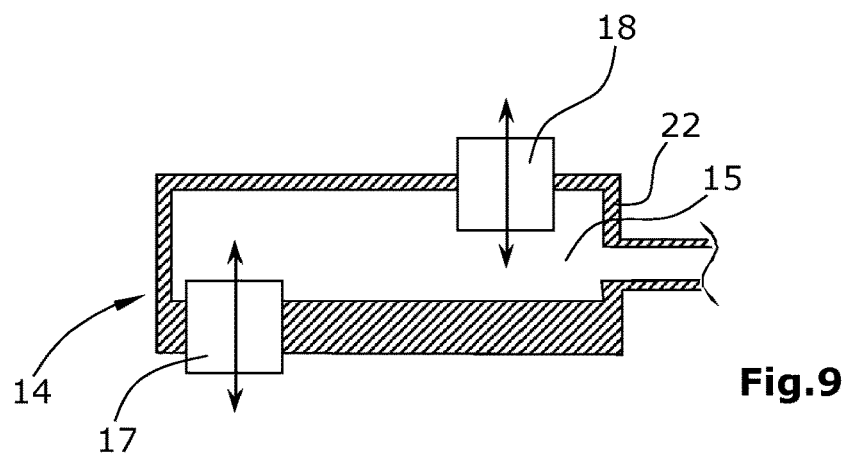

In FIG. 9 the force is transmitted from an external drive to the functional element 12 not illustrated via the pressure transmission device 14. For this purpose, a first plunger 17 is provided which acts upon the fluid 15 inside the housing 22. This fluid, in turn, generates a pressure acting upon an element not illustrated which is coupled with the functional element 12. When uncoupling the instrument 10 from the medical robot, the first plunger 17 must be stopped such that the operating element 18, which is also configured as a plunger acting upon the fluid 15, can manually actuate the functional element 12.

The embodiment shown in FIG. 10 has already been explained in conjunction with FIG. 4. The electric and/or electronic operating element 18 illustrated here may be a switch, a button, a joystick, a potentiometer, a scroll wheel etc. which is connected with the internal drive 30 via a signal connection 58. In this embodiment, the instrument 10 may comprise a power supply unit, for example a battery, an accumulator or a capacitor etc., to ensure functioning of the instrument, at least for a short period, even in the state in which the instrument is uncoupled from the robot.

The invention claimed is:

1. A minimally invasive instrument for robotic surgery comprising:
   a functional element disposed at a distal end of the instrument for performing a surgical operation;
   a transmission device operatively coupled to the functional element for directly transmitting at least one of force, torque and pressure thereto;
   a drive coupled to the transmission device for mechanically actuating the functional element by at least one of force, torque and pressure;
   an operating element coupled to the transmission device for manually operating the functional element by at least one of force, torque and pressure;
   a medical robot for performing robotic surgery; and
   a device for releasably coupling the instrument to the medical robot, such that when the instrument is coupled to the robot, the drive is configured to mechanically actuate the functional element, and when the instrument is uncoupled from the robot, the operating element is configured to actuate the functional element.

2. The instrument of claim 1, wherein the functional element is at least one of a gripper, a needle holder and scissors.

3. A minimally invasive instrument for robotic surgery comprising:
   a functional element disposed at a distal end of the instrument for performing a surgical operation;
   a transmission device operatively coupled to the functional element for directly transmitting at least one of force, torque, and pressure thereto;
   a drive coupled to the transmission device for mechanically actuating the functional element by at least one of force, torque and pressure;
   an operating element coupled to the transmission device for manually operating the functional element by at least one of force, torque and pressure;
   a medical robot for performing robotic surgery; and
   a device for releasably coupling the instrument to the medical robot.

* * * * *